United States Patent
Cao et al.

(10) Patent No.: US 11,925,379 B2
(45) Date of Patent: Mar. 12, 2024

(54) TORQUE WRENCH FOR ULTRASONIC SCALPEL, AND ULTRASONIC SCALPEL/TORQUE WRENCH SET

(71) Applicant: Beijing SMTP Technology Co., Ltd., Beijing (CN)

(72) Inventors: Qun Cao, Beijing (CN); Zhen Feng, Beijing (CN); Songtao Zhan, Beijing (CN)

(73) Assignee: BEIJING SMTP TECHNOLOGY CO., LTD., Beijing (CN)

( * ) Notice: Subject to any disclaimer, the term of this patent is extended or adjusted under 35 U.S.C. 154(b) by 649 days.

(21) Appl. No.: 17/252,685

(22) PCT Filed: Jul. 8, 2019

(86) PCT No.: PCT/CN2019/095057
§ 371 (c)(1),
(2) Date: Dec. 15, 2020

(87) PCT Pub. No.: WO2019/238141
PCT Pub. Date: Dec. 19, 2019

(65) Prior Publication Data
US 2021/0307777 A1    Oct. 7, 2021

(30) Foreign Application Priority Data

Jul. 25, 2018 (CN) .......................... 201821183432.0

(51) Int. Cl.
*A61B 17/32* (2006.01)
*A61B 17/00* (2006.01)
(Continued)

(52) U.S. Cl.
CPC .. *A61B 17/320068* (2013.01); *A61B 17/3211* (2013.01); *A61B 90/03* (2016.02);
(Continued)

(58) Field of Classification Search
CPC ........ A61B 17/320068; A61B 17/3211; A61B 2017/320082; A61B 2017/320075;
(Continued)

(56) References Cited

U.S. PATENT DOCUMENTS 5,059,210 A * 10/1991 Clark ................. A61B 17/3215
464/37
5,511,451 A 4/1996 Steen et al.
(Continued)

FOREIGN PATENT DOCUMENTS

CN    201070394    6/2008
CN    102413784    4/2012
(Continued)

OTHER PUBLICATIONS

PCT/CN2019/095057 , "International Preliminary Report on Patentability", dated Feb. 4, 2021, 10 pages.
(Continued)

*Primary Examiner* — Hadi Shakeri
(74) *Attorney, Agent, or Firm* — Kilpatrick Townsend & Stockton LLP

(57) ABSTRACT

A torque wrench for an ultrasonic scalpel, the torque wrench comprising a torque wrench body and a wrench rotor. The torque wrench body comprises a circular-hole-shaped torque hole, with a torque clamping catch being provided in the torque hole, and the wrench rotor being disposed in the torque hole. The wrench rotor comprises a scalpel head clamping hole, a rotor clamping catch located outside the wrench rotor, and a scalpel head clamping slot located inside the scalpel head clamping hole, wherein a wrench part, which is disposed on a scalpel head of the ultrasonic scalpel that is fitted with the torque wrench of the ultrasonic scalpel, (Continued)

is clamped into the scalpel head clamping slot via the scalpel head clamping hole, the rotor clamping catch is fitted with the torque clamping catch.

16 Claims, 6 Drawing Sheets

(51) Int. Cl.
　　*A61B 17/3211* (2006.01)
　　*A61B 90/00* (2016.01)
　　*B25B 13/50* (2006.01)

(52) U.S. Cl.
　　CPC .... *B25B 13/50* (2013.01); *A61B 2017/00477* (2013.01); *A61B 2017/320075* (2017.08); *A61B 2017/320082* (2017.08); *A61B 2090/031* (2016.02)

(58) Field of Classification Search
　　CPC .......... A61B 2017/00477; A61B 90/03; A61B 2090/031; B25B 13/50; B25B 23/1427
　　USPC ................................................ 81/176.15, 475
　　See application file for complete search history.

(56) References Cited

U.S. PATENT DOCUMENTS

| | | | |
|---|---|---|---|
| 6,439,086 B1 * | 8/2002 | Bahr | B25B 23/141 81/473 |
| 6,928,907 B2 | 8/2005 | Casabonne et al. | |
| 7,159,494 B2 * | 1/2007 | Jamnia | B25B 23/1427 81/472 |
| 9,868,194 B2 * | 1/2018 | Ivinson | F16D 43/2026 |
| 11,283,217 B2 * | 3/2022 | Montena | H01R 9/05 |
| 2004/0055425 A1 | 3/2004 | Casabonne et al. | |
| 2006/0123958 A1 | 6/2006 | Jamnia et al. | |

FOREIGN PATENT DOCUMENTS

| | | |
|---|---|---|
| CN | 103120596 | 5/2013 |
| CN | 203369938 | 1/2014 |
| CN | 205831876 | 12/2016 |
| CN | 206303948 | 7/2017 |
| CN | 107095722 | 8/2017 |
| CN | 206979534 | 2/2018 |
| CN | 208697287 | 4/2019 |
| EP | 1671751 A1 | 6/2006 |
| EP | 1946708 A2 | 7/2008 |
| JP | 0534025 A | 2/1993 |
| JP | 06507791 A | 9/1994 |
| JP | 2004514513 A | 5/2004 |
| JP | 2013526965 A | 6/2013 |
| KR | 20070072870 A | 7/2007 |
| KR | 20180072721 A | 6/2018 |
| WO | 2007143439 A2 | 12/2007 |
| WO | 2014164293 | 10/2014 |

OTHER PUBLICATIONS

PCT/CN2019/095057, "International Search Report and Written Opinion", dated Oct. 22, 2019, 12 pages.

KR10-2021-7002458, "Notice of Allowance", dated Jul. 19, 2023, 4 pages.

* cited by examiner

TORQUE WRENCH FOR ULTRASONIC SCALPEL, AND ULTRASONIC SCALPEL/TORQUE WRENCH SET

CROSS-REFERENCE TO RELATED APPLICATIONS

This application is a U.S. National Stage of International Application No. PCT/CN2019/095057, filed Jul. 8, 2019, which claims the benefit of Chinese Patent Application No. 201821183432.0, titled "TORQUE WRENCH FOR ULTRASONIC SCALPEL" filed Jul. 25, 2018. The contents of the applications are hereby incorporated by reference in their entireties for all purposes.

TECHNICAL FIELD

The present disclosure relates to the technical field of medical instruments, and in particular to a torque wrench for an ultrasonic scalpel, and an ultrasonic scalpel and torque wrench set.

BACKGROUND ART

In surgery, an ultrasonic scalpel is often used for cutting and reconstruction of soft tissue, hard tissue and human tissue. For the convenience of use, a handle and a scalpel head of a surgical ultrasonic scalpel use a separate design and are connected by threads. During the connection process, the scalpel head needs to be fastened to the handle by a wrench.

In order to prevent the excessive securing of the scalpel head during the securing, a torque wrench is often used for securing. However, most of the conventional torque wrenches can only adapt to a scalpel head with a straight bar, and cannot be used when the scalpel head is bent at an angle or is an irregular-shaped scalpel head.

SUMMARY OF THE INVENTION

The purpose of the present disclosure is to provide a torque wrench for an ultrasonic scalpel, the torque wrench for an ultrasonic scalpel comprising a torque wrench body and a wrench rotor, wherein the torque wrench body comprises a circular-hole-shaped torque hole, with a torque clamping catch being provided in the torque hole, and the wrench rotor being disposed in the torque hole; and the wrench rotor comprises a scalpel head clamping hole, a rotor clamping catch located outside the wrench rotor, and a scalpel head clamping slot located inside the scalpel head clamping hole, a wrench part, which is disposed on a scalpel head of the ultrasonic scalpel that is fitted with the torque wrench of the ultrasonic scalpel, is clamped into the scalpel head clamping slot via the scalpel head clamping hole, the rotor clamping catch is fitted with the torque clamping catch, the torque hole has a cylindrical structure with gradually expanding radius, and the wrench rotor is disposed in an end portion, with a smaller diameter, of the torque hole.

BRIEF DESCRIPTION OF THE DRAWINGS

In order to illustrate the technical solutions in the particular embodiments of the present disclosure or in the prior art more clearly, the accompanying drawings to be used in the description of the particular embodiments or the prior art will be briefly introduced below; obviously, the accompanying drawings in the following description show some of the embodiments of the present disclosure, and those of ordinary skill in the art may still derive other drawings from these accompanying drawings without creative effort.

DETAILED DESCRIPTION OF EMBODIMENTS

Figure 1:
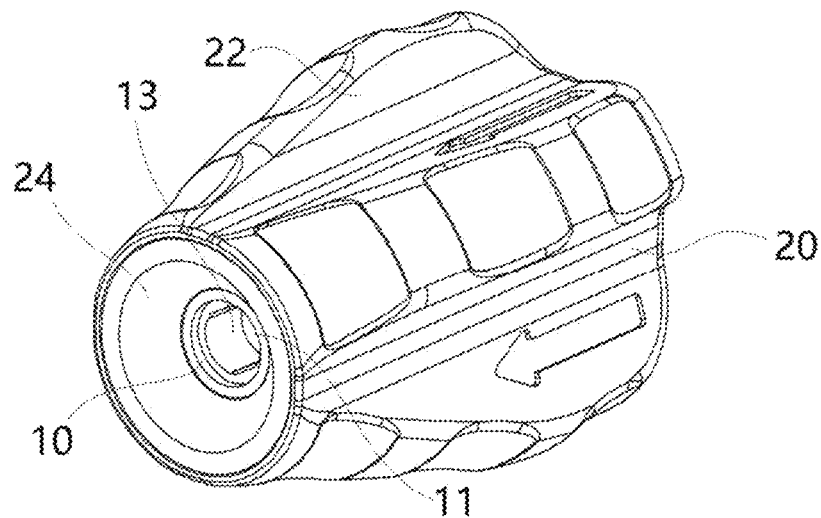
FIG. 1 is a perspective view of a torque wrench for an ultrasonic scalpel according to a first embodiment of the present disclosure.

In order to make the objectives, technical solutions and advantages of the present disclosure clearer, the technical solutions in the embodiments of the present disclosure will be clearly and completely described with reference to the accompanying drawings in the embodiments of the present disclosure. It should be understood that the specific embodiments described herein are merely illustrative of the present disclosure, but are not intended to limit the present disclosure. The embodiments described are merely some, rather than all, of the embodiments of the present disclosure. All other embodiments obtained by those of ordinary skill in the art based on the embodiments of the present disclosure without any creative effort shall fall within the protection scope of the present disclosure.

In the description of the present disclosure, it should be noted that the orientation or position relationship indicated by the terms "upper", "lower", etc. are based on the orientation or position relationship shown in the accompanying drawings, are intended to facilitate the description of the present disclosure and simplify the description only, rather than indicating or implying that the devices or elements referred to must have particular orientations or be constructed and operated in particular orientations, and will not to be interpreted as limiting the present disclosure. Among them, "inner" and "outer" are relative to the hole, that is, "inner" refers to the direction toward the inner cavity of the hole, and "outer" refers to the direction away from the inner cavity of the hole and is the reverse direction to "inner".

Furthermore, in the description of the present disclosure, it should be noted that the terms "connecting" and "connection" should be understood in a broad sense, unless otherwise explicitly specified or defined, for example, the connection may be a fixed connection, a detachable connection or an integrated connection, may be a mechanical connection or an electrical connection, may also be a direct connection or an indirect connection through an intermediate medium, or may be the communication between the interior of two elements. For those of ordinary skill in the art, the specific meanings of the terms mentioned above in the present disclosure should be construed according to specific circumstances.

FIGS. 1 to 4 and FIGS. 7 to 15 show a torque wrench for an ultrasonic scalpel according to the present disclosure. A torque wrench for an ultrasonic scalpel in present disclosure comprises a torque wrench body 20 and a wrench rotor 10. The torque wrench body 20 comprises a circular-hole-shaped torque hole 21, with a torque clamping catch being provided in the torque hole 21, and the wrench rotor 10 being disposed in the torque hole 21. The wrench rotor 10 comprises a scalpel head clamping hole 11, a rotor clamping catch 12 located outside the wrench rotor 10, and a scalpel head clamping slot 13 located inside the scalpel head clamping hole 11. A wrench part 31, which is disposed on a scalpel head 30 of the ultrasonic scalpel that is fitted with the torque wrench of the ultrasonic scalpel, is clamped into the scalpel head clamping slot 13 via the scalpel head clamping hole 11, and the rotor clamping catch 12 is fitted with the torque clamping catch.

The torque wrench for an ultrasonic scalpel according to the present disclosure comprises a wrench rotor 10 and a torque wrench body 20, wherein the torque wrench body 20 comprises a torque clamping catch, the wrench rotor 10 comprises a rotor clamping catch 12 and a scalpel head clamping hole 11, the rotor clamping catch 12 is fitted with the torque clamping catch, the scalpel head of the ultrasonic scalpel is provided with a wrench part 31, and the scalpel head clamping hole 11 is fitted with the wrench part 31. By means of individually providing the wrench rotor 10, the wrench rotor 10 is fitted with the torque clamping catch of the torque wrench body 20, such that different types of scalpel heads 30 of an ultrasonic scalpel can be clamped in the scalpel head clamping hole 11 without affecting the fitting between the rotor clamping catch 12 and the torque clamping catch. Therefore, the torque wrench for an ultrasonic scalpel can provide the function of mounting various ultrasonic scalpel heads, thereby increasing the application range of the torque wrench and improving the convenience of use.

FIGS. 1 to 4 show the torque wrench for an ultrasonic scalpel according to the first embodiment of the present disclosure. The torque wrench body 20 has a cylindrical structure with gradually expanding radius, the cylindrical structure comprises a large end and a small end, the wrench rotor 10 is disposed in the small end, the torque wrench body 20 further comprises a plurality of torque hand-holding portions 22 extending from the small end to the large end, and the plurality of torque hand-holding portions 22 protrude outward from an outer wall of the torque wrench body 20 and are evenly distributed in a circumferential direction with the torque hole 21 as the center. The torque wrench body 20 is designed to have a cylindrical structure with gradually expanding radius, which facilitates the scalpel head 30 with different shapes at the front end (especially the scalpel head with a curved front end or the irregular-shaped scalpel head) to smoothly pass through the wrench rotor 10, such that the wrench part 31 of the scalpel head 30 can smoothly reach to the inside of the wrench rotor 10 and is fitted with the scalpel head clamping hole 11 of the wrench rotor 10. In the preferred embodiment of the present disclosure, the diameter of the torque hole 21 at the small end is smaller than the diameter of the torque hole 21 at the large end, that is, the torque hole 21 has a cylindrical structure with gradually expanding radius. The torque hole 21 is designed to have a cylindrical structure with gradually expanding radius, which facilitates the scalpel head 30 with different shapes at the front end (especially the scalpel head with a curved front end or the irregular-shaped scalpel head) to smoothly pass through the wrench rotor 10, such that the wrench part 31 of the scalpel head 30 can smoothly reach to the inside of the wrench rotor 10 and be fitted with the scalpel head clamping hole 11 of the wrench rotor 10. As such, the scalpel head 30 of the ultrasonic scalpel with a certain bending angle can pass through, and during the installation or disassembly, the scalpel head 30 of the ultrasonic scalpel will not interfere with the installation of the torque wrench body 20, such that the torque wrench for an ultrasonic scalpel can provide the function of mounting various ultrasonic scalpel heads, thereby increasing the application range of the torque wrench and improving the convenience of use. In a non-limiting manner, the torque wrench body 20 may also be a prism or cone with gradually increasing cross-sectional area. The outer wall of the torque wrench body 20 further comprises a plurality of outwardly protruding torque hand-holding portions 22, which is used for an operator to hold the torque wrench body 20 and conveniently apply a force to turn the torque wrench body 20. Preferably, the plurality of torque hand-holding portions 22 may be provided, on the surface thereof, with a non-slip surface to further facilitate the holding by an operator. As shown in FIGS. 1 to 4, the outer wall of the torque wrench body 20 is provided with four torque hand-holding portions 22, and preferably, the two side walls of the torque hand-holding portions 22 are arc-shaped and gradually converge in a radial direction from the central axis of the torque wrench body 20 to the circumference so as to be more suitable for holding by hand.

Figure 2:
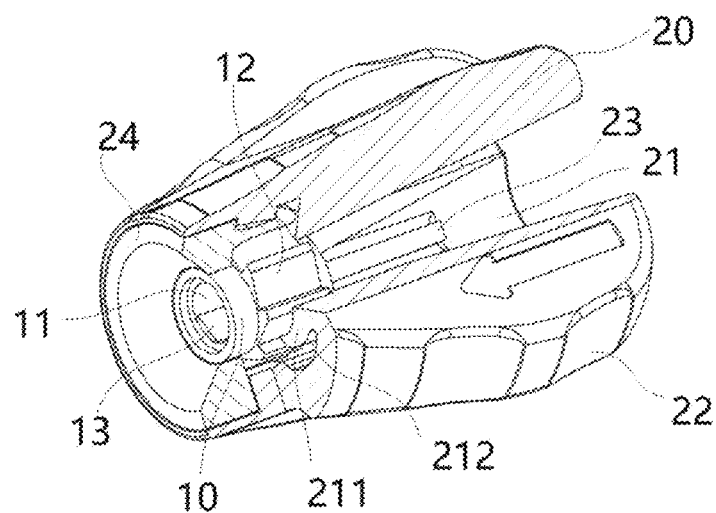
FIG. 2 is a partial cross-sectional view of the torque wrench for an ultrasonic scalpel according to the first embodiment of the present disclosure.
Figure 3:
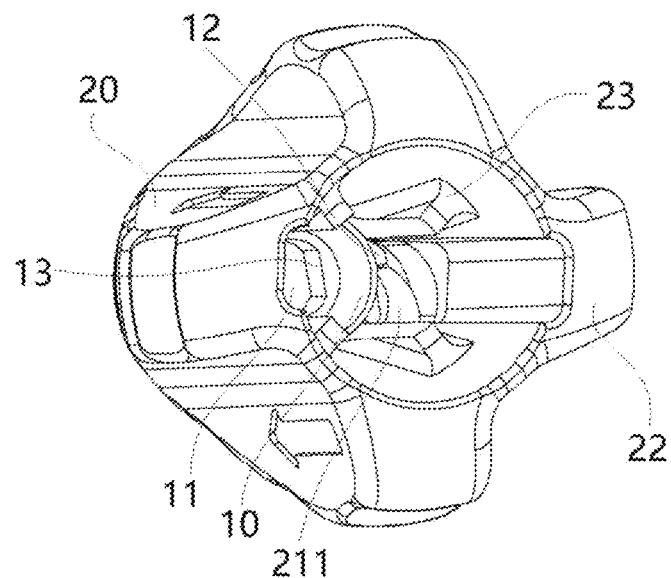
FIG. 3 is a perspective view of a left end of the torque wrench for an ultrasonic scalpel according to the first embodiment of the present disclosure.
Figure 4:
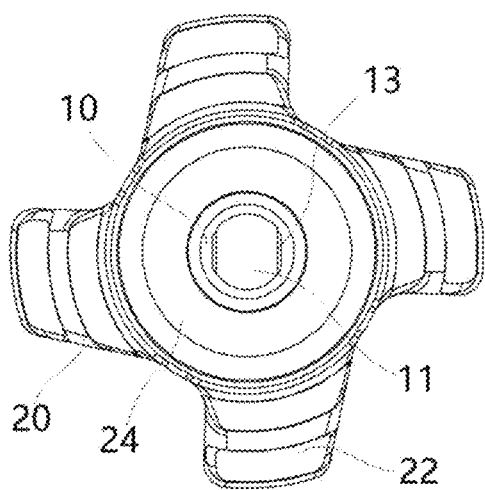
FIG. 4 is a right side view of the torque wrench for an ultrasonic scalpel according to the first embodiment of the present disclosure.

As shown in FIGS. 2 and 3, the inner wall of the torque hole 21 further comprises a plurality of limiting bulges 23, and the plurality of limiting bulges 23 may correspond to the positions of the plurality of torque hand-holding portions 22 on a one-to-one basis. The plurality of limiting bulges 23 are evenly distributed in the circumferential direction with the torque hole 21 as the center, and the diameter of the largest circle formed by the plurality of limiting bulges 23 is smaller than the diameter of the handle 40 of the ultrasonic scalpel.

According to the first embodiment of the present disclosure, the limiting bulges 23 are prism-shaped.

Figure 5:
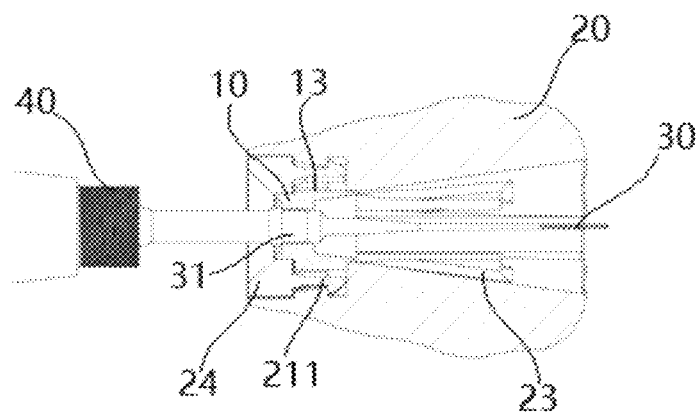
FIG. 5 is a side cross-sectional view of the fitting between the torque wrench for an ultrasonic scalpel and a wrench part of the ultrasonic scalpel according to the first embodiment of the present disclosure.
Figure 6:
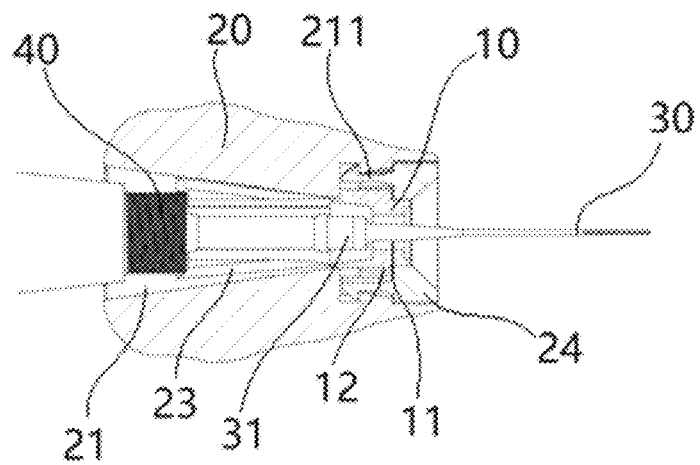
FIG. 6 is a side cross-sectional view showing that the torque wrench for an ultrasonic scalpel cannot be fitted with the wrench part of the ultrasonic scalpel when the torque wrench for the ultrasonic scalpel according to the first embodiment of the present disclosure is used in a reverse direction.

As shown in FIGS. 5 and 6, the wrench rotor 10 comprises a wrench part engagement portion and an expansion portion, with the length of the wrench part engagement portion along the central axis of the torque wrench body being substantially equal to the length of the wrench part, the expansion portion being adjacent to the limiting bulge 23 (that is, the expansion portion being located between the wrench part engagement portion and the limiting bulge 23), and the size of the inner hole of the expansion portion being larger than that of the inner hole of the wrench part engagement portion. Preferably, the inner hole of the expansion portion also has a cylindrical structure with gradually expanding radius, and the inner hole of the expansion portion and the torque hole 21 form a substantially frustoconical hole.

Still referring to FIGS. 5 and 6, an end face, away from the wrench rotor 10, of the limiting bulge 23 and an end face, close to the limiting bulge 23, of the wrench part engagement portion of the wrench rotor 10 are spaced apart by a first distance therebetween along the central axis of the torque wrench body 20, and an end face, close to the wrench part, of the handle 40 of the ultrasonic scalpel and an end face, away from the handle 40, of the wrench part 31 are spaced apart by a second distance along the central axis of the torque wrench body 20, the first distance is greater than the second distance, such that when the ultrasonic scalpel is inserted into the torque wrench in a direction from the end face, away from the wrench rotor 10, of the limiting bulge 23 to the wrench part 31, the wrench part 31 is unable to reach the inside of the wrench rotor 10. Therefore, when the torque wrench is used in a reverse direction, the limiting bulge 23 will stop the handle 40 of the ultrasonic scalpel, such that the wrench part 31 of the scalpel head 30 cannot reach the inside of the wrench rotor 10, that is, the wrench part 31 of the scalpel head 30 cannot be fitted with the scalpel head clamping hole 11 of the wrench rotor 10, thereby avoiding the use of the torque wrench in the reverse direction. That is, the anti-reverse connection design of the torque wrench can functionally prevent the torque wrench from being used in the reverse direction to prevent errors in use, thereby improving the efficiency and convenience of use.

FIG. 3 shows the structure of the torque clamping catch of the torque wrench for an ultrasonic scalpel according to the first embodiment of the present disclosure. Specifically, the torque clamping catch comprises a plurality of unidirectional raised catches 211 protruding from an inner wall of the torque hole 21 to the center of the torque hole 21, and the plurality of the unidirectional raised catches 211 are annularly distributed on the inner wall of the torque hole 21. As such, the plurality of unidirectional raised catches 211 and the rotor clamping catch 12 are fitted with each other, such that the torque wrench for the ultrasonic scalpel can apply torque to the scalpel head of the ultrasonic scalpel. In order to facilitate the fitting between the unidirectional raised catches 211 and the rotor clamping catch 12, in particular, the torque clamping catch comprises at least two unidirectional raised catches 211, such that the unidirectional raised catches 211 and the rotor clamping catch 12 can be quickly fitted with each other. Herein, the unidirectional raised catches 211 are raised catches with a catch tip being inclined toward one side. Such unidirectional raised catches 211 can be easily and quickly fitted with the rotor clamping catch 12, and are convenient for the torque wrench to apply torque, so as to prevent the unidirectional raised catches 211 from being disengaged from the rotor clamping catch 12. As shown in FIG. 3, the catch tips of the plurality of unidirectional raised catches 211 are inclined within the circular-hole-shaped torque hole 21 in a clockwise direction to form a ring shape. Of course, the present disclosure is not limited to this, and the catch tips of the plurality of unidirectional raised catches 211 may also be inclined within the circular-hole-shaped torque hole 21 in a counterclockwise direction to form a ring shape.

For the better distribution of the plurality of unidirectional raised catches 211 to form a ring shape, both side walls of each unidirectional raised catch 211 can be designed as arc-shaped and gradually converge from the inner wall of the torque hole 21 to the center of the torque hole 21 so as to from the unidirectional raised catch 211 with a catch tip being inclined toward one side. As shown in FIG. 3, the shape of the unidirectional raised catches 211 is similar to the crescent shape.

When the plurality of unidirectional raised catches 211 are fitted with the rotor clamping catch 12, the unidirectional raised catches 211 will deform when torque is applied to the torque wrench, and thus it is necessary to leave a deformation space for the deformation of the unidirectional raised catches 211. In a preferred embodiment of the present disclosure, as shown in FIG. 3, the torque wrench body 20 further comprises a groove 212 that corresponds to the gradually changing profile of the unidirectional raised catches 211 to form on the inner wall of the torque hole 21.

Preferably, two side walls of the groove 212 are also arc-shaped and gradually converge in a direction opposite to the direction in which the two side walls of the unidirectional raised catches 211 gradually converge. The converging direction of the two side walls of the groove 212 is opposite to the converging direction of the two side walls of the unidirectional raised catches 211, such that the unidirectional raised catches 211 gradually expand in a direction away from the center of the torque hole 21, so as to ensure the strength of the unidirectional raised catches 211 and also leave a deformation space for the deformation of the unidirectional raised catches 211.

In a preferred embodiment of the present disclosure, the torque wrench body 20 further comprises a clamping wheel 24, the clamping wheel 24 is detachably clamped in the torque hole 21, the wrench rotor 10 is disposed in the clamping wheel 24, the torque clamping catch is formed on an inner wall of the clamping wheel 24, and the rotor clamping catch 12 is fitted with the torque clamping catch. Specifically, referring to FIGS. 2 and 5, the inner wall of the torque wrench body 20 is provided with a clamping slot, and the outer wall of the clamping wheel 24 is circumferentially provided with a hook that is fitted with the clamping slot, such that the clamping wheel 24 is detachably clamped in the torque hole 21. Therefore, in the torque hole 21, the rotor clamping catch 12 of the wrench rotor 10 is fitted with the torque clamping catch provided on the inner wall of the clamping wheel 24. As such, the components of the torque wrench can be conveniently replaced without replacing the whole torque wrench. For example, by means of replacing the wrench rotor 10 having a scalpel head clamping hole 11 of different shapes and/or sizes, the torque wrench according to the present disclosure can be used for ultrasonic scalpels having a wrench part of various shapes and/or sizes.

In a preferred embodiment of the present disclosure, as shown in FIG. 2, the rotor clamping catch 12 is disposed on an outer circumferential surface of the wrench rotor 10, and the cross section of the clamping catch 12 is of a unidirectional ratchet shape. The unidirectional raised catches 211 of the torque wrench are respectively fitted with the rotor clamping catch 12. After the unidirectional ratchet-shaped rotor clamping catch 12 and the torque clamping catches (i.e., unidirectional raised catches 211) of the torque wrench are fitted with each other, when the torque wrench body 20 is turned towards the torque application direction (securing the scalpel head), it is necessary to overcome the predetermined force of the torque clamping catch, and when the predetermined force is exceeded, the torque clamping catch will deform and be disengaged by rotation, so as to secure the scalpel head with a constant force; and when the torque wrench body 20 is turned in a resistance direction (removing the scalpel head), which is a pure resistance state in the case of engagement, the torque clamping catch will not deform when rotating in this direction, and thus the scalpel head can be removed by rotating at the maximum torque value.

Figure 7:
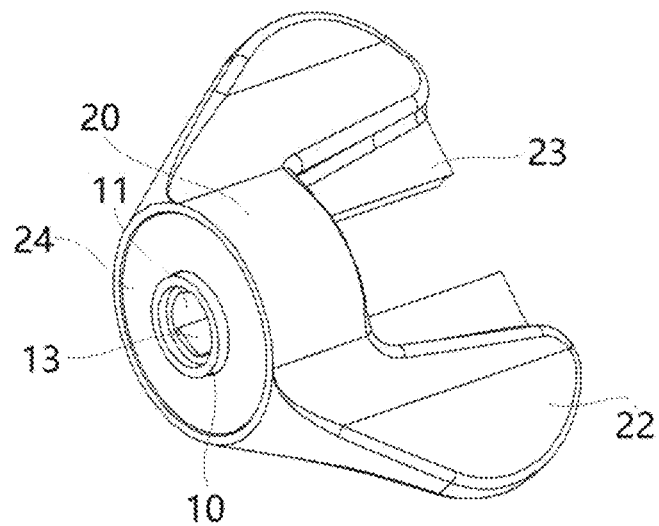
FIG. 7 is a perspective view of a torque wrench for an ultrasonic scalpel according to a second embodiment of the present disclosure.
Figure 8:
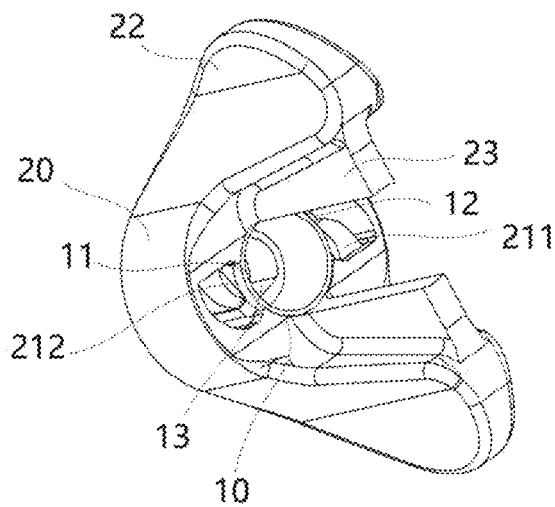
FIG. 8 is a perspective view of a right end of the torque wrench for an ultrasonic scalpel according to the second embodiment of the present disclosure.
Figure 9:
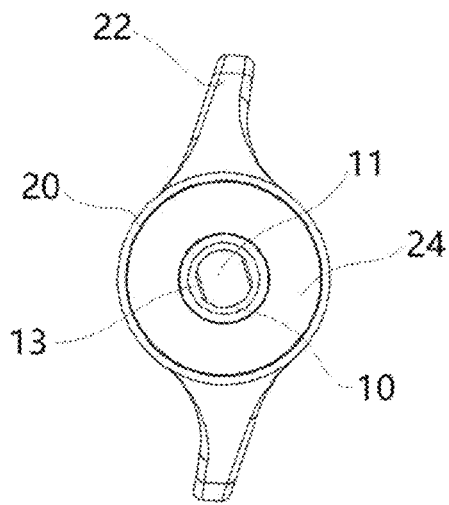
FIG. 9 is a left side view of the torque wrench for an ultrasonic scalpel according to the second embodiment of the present disclosure.

FIGS. 7 to 8 show the torque wrench for an ultrasonic scalpel according to a second embodiment of the present disclosure. The difference from the torque wrench for an ultrasonic scalpel according to the first embodiment is in that the torque wrench for an ultrasonic scalpel according to the second embodiment comprises two torque hand-holding portions 22, and the two side walls of the torque hand-holding portion 22 are arc-shaped and gradually converge in a radial direction from the central axis of the torque wrench body 20 to the circumference. Moreover, the torque wrench body 20 has a cylindrical structure with gradually expanding radius, and the cylindrical structure between the two torque hand-holding portions 22 is removed, such that the structure of the torque wrench is simpler, and the production cost can be reduced.

Figure 10:
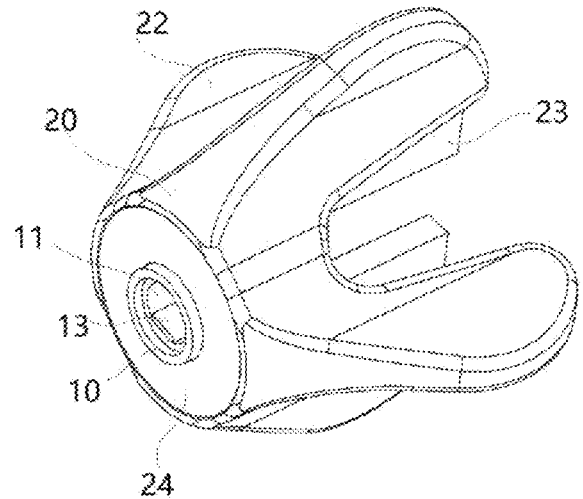
FIG. 10 is a perspective view of a torque wrench for an ultrasonic scalpel according to a third embodiment of the present disclosure.
Figure 11:
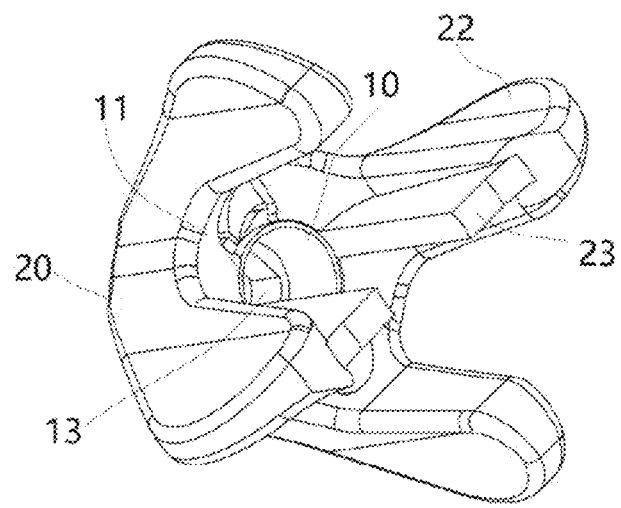
FIG. 11 is a perspective view of a right end of the torque wrench for an ultrasonic scalpel according to the third embodiment of the present disclosure.
Figure 12:
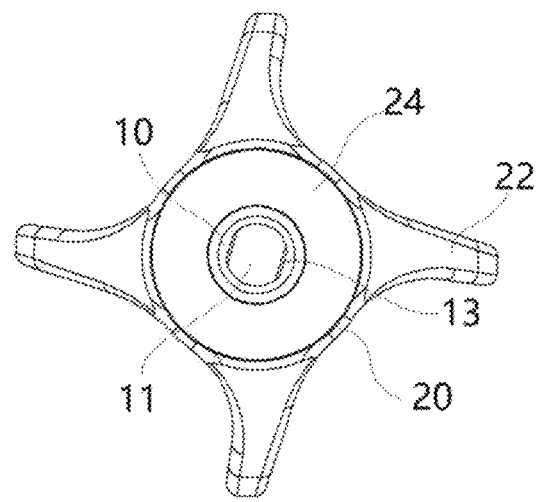
FIG. 12 is a left side view of the torque wrench for an ultrasonic scalpel according to the third embodiment of the present disclosure.

FIGS. 10 to 12 show the torque wrench for an ultrasonic scalpel according to a third embodiment of the present disclosure. The third embodiment of the present disclosure differs from the torque wrench for an ultrasonic scalpel according to the second embodiment in that the torque wrench for an ultrasonic scalpel according to the third embodiment comprises four torque hand-holding portions 22, the two side walls of the torque hand-holding portion 22 are arc-shaped and gradually converge in a direction opposite to the direction from the inner wall of the torque hole 21 to the center of the torque hole 21. Similarly, the torque wrench body 20 has a cylindrical structure with gradually expanding radius, and the portion between the two torque hand-holding portions 22 is removed, such that the structure of the torque wrench is simpler, and the production cost can be reduced.

Figure 13:
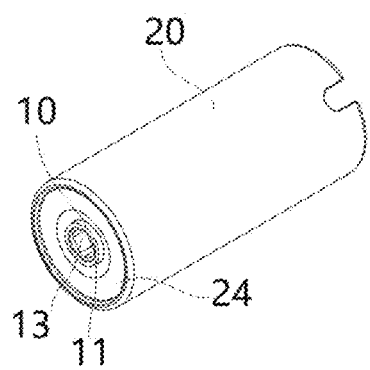
FIG. 13 is a perspective view of a torque wrench for an ultrasonic scalpel according to a fourth embodiment of the present disclosure.
Figure 14:
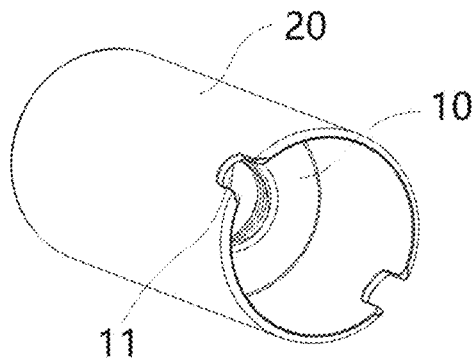
FIG. 14 is a perspective view of a right end of the torque wrench for an ultrasonic scalpel according to the fourth embodiment of the present disclosure.
Figure 15:
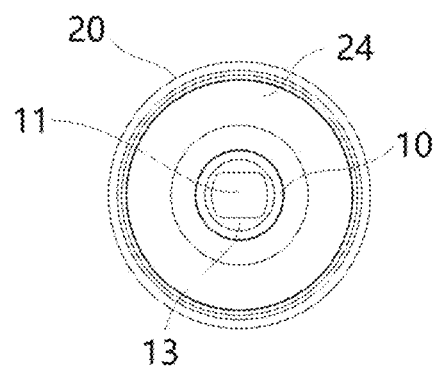
FIG. 15 is a left side view of the torque wrench for an ultrasonic scalpel according to the fourth embodiment of the present disclosure.

FIGS. 13 to 15 show the torque wrench for an ultrasonic scalpel according to a fourth embodiment of the present disclosure. The torque wrench for the ultrasonic scalpel according to the fourth embodiment of the present disclosure differs from the torque wrench for an ultrasonic scalpel according to the first embodiment in that the torque wrench body 20 of the torque wrench for an ultrasonic scalpel according to the fourth embodiment uses a long cylindrical structure to meet the needs of holding by a whole hand, the operation is more comfortable, improving the user-friendliness of the torque wrench for an ultrasonic scalpel.

As shown in FIG. 5, the scalpel head 30 for an ultrasonic scalpel may be provided with a thread structure connected to the handle 40, and the scalpel head 30 is provided with a wrench part 31. The torque clamping catch is fitted with the rotor clamping catch 12, and then torque is applied to the torque wrench body 20 of the torque wrench, such that the scalpel head 30 is in threaded connection with the handle 40. As such, the installation and disassembly of the scalpel head for an ultrasonic scalpel are achieved.

In conclusion, the torque wrench for an ultrasonic scalpel according to the present disclosure comprises a wrench rotor 10 and a torque wrench body 20, wherein the torque wrench body 20 comprises a torque clamping catch, the wrench rotor 10 comprises a rotor clamping catch 12 and a scalpel head clamping hole 11, the rotor clamping catch 12 is fitted with the torque clamping catch, the scalpel head of the ultrasonic scalpel is provided with a wrench part 31, and the scalpel head clamping hole 11 is fitted with the wrench part 31. By means of individually providing the wrench rotor 10, the wrench rotor 10 is fitted with the torque clamping catch of the torque wrench body 20, such that different types of scalpel heads 30 of an ultrasonic scalpel can be clamped in the scalpel head clamping hole 11 without affecting the fitting between the rotor clamping catch 12 and the torque clamping catch. Therefore, the torque wrench for an ultrasonic scalpel can provide the function of mounting various ultrasonic scalpel heads, thereby increasing the application range of the torque wrench and improving the convenience of use.

The present disclosure further provides an ultrasonic scalpel and torque wrench set, in which the wrench part of the ultrasonic scalpel is fitted in shape with the wrench rotor of the torque wrench, so as to secure the ultrasonic scalpel with the torque wrench.

The above description are merely the specific embodiments of the present disclosure, but the scope of protection of the present disclosure is not limited thereto, and any changes or substitutions readily made by those skilled in the art within the technical scope disclosed in the present disclosure should all be intended to be included within the scope of protection of the present disclosure.

The invention claimed is:

1. A torque wrench for an ultrasonic scalpel, comprising a torque wrench body and a wrench rotor, wherein the torque wrench body comprises a circular-hole-shaped torque hole, with a torque clamping catch being provided in the torque hole, and the wrench rotor being disposed in the torque hole; and the wrench rotor comprises a scalpel head clamping hole, a rotor clamping catch located outside the wrench rotor, and a scalpel head clamping slot located inside the scalpel head clamping hole;

a wrench part, which is disposed on a scalpel head of the ultrasonic scalpel that is fitted with the torque wrench for the ultrasonic scalpel, is clamped into the scalpel head clamping slot via the scalpel head clamping hole, the rotor clamping catch is fitted with the torque clamping catch, the torque hole has a cylindrical structure with gradually expanding radius, and the wrench rotor is disposed in an end portion, with a smaller diameter, of the torque hole wherein, the torque wrench body has a cylindrical structure with gradually expanding radius, the cylindrical structure comprises a large end and a small end, the wrench rotor is disposed in the small end, the torque wrench body further comprises a plurality of torque hand-holding portions extending from the small end to the large end, and the plurality of torque hand-holding portions protrude outward from an outer wall of the torque wrench body and are evenly distributed in a circumferential direction with the torque hole as the center; and an inner wall of the torque hole further comprises a plurality of limiting bulges, the plurality of limiting bulges are evenly distributed in the circumferential direction with the torque hole as the center, and the diameter of the largest circle formed by the plurality of limiting bulges is smaller than the diameter of a handle of the ultrasonic scalpel.

2. The torque wrench for an ultrasonic scalpel according to claim 1, wherein
the torque clamping catch comprises a plurality of unidirectional raised catches protruding from an inner wall of the torque hole to the center of the torque hole, and the plurality of the unidirectional raised catches are annularly distributed on the inner wall of the torque hole.

3. The torque wrench for an ultrasonic scalpel according to claim 2, wherein
two side walls of the unidirectional raised catches are both arc-shaped and gradually converge from the inner wall of the torque hole to the center of the torque hole.

4. The torque wrench for an ultrasonic scalpel according to claim 2, wherein
the torque wrench body further comprises a groove corresponding to a gradually changing profile of the unidirectional raised catches and formed on the inner wall of the torque hole.

5. The torque wrench for an ultrasonic scalpel according to claim 4, wherein
two side walls of the groove are also arc-shaped and gradually converge in a direction opposite to the direction in which the two side walls of the unidirectional raised catches gradually converge.

6. The torque wrench for an ultrasonic scalpel according to claim 1, wherein
the torque wrench body further comprises a clamping wheel, the clamping wheel is detachably clamped in the torque hole, the wrench rotor is disposed in the clamping wheel, the torque clamping catch is formed on an inner wall of the clamping wheel, and the rotor clamping catch is fitted with the torque clamping catch.

7. The torque wrench for an ultrasonic scalpel according to claim 6, wherein
the inner wall of the torque wrench body is provided with a clamping slot, and the outer wall of the clamping wheel is circumferentially provided with a hook that is fitted with the clamping slot, such that the clamping wheel is detachably clamped in the torque hole.

8. The torque wrench for an ultrasonic scalpel according to claim 1, wherein
the rotor clamping catch is disposed on an outer circumferential surface of the wrench rotor, and the cross section of the rotor clamping catch is of a unidirectional ratchet shape.

9. The torque wrench for an ultrasonic scalpel according to claim 1, wherein
the diameter of the torque hole located at the small end is smaller than the diameter of the torque hole located at the large end.

10. The torque wrench for an ultrasonic scalpel according to claim 1, wherein the wrench rotor comprises a wrench part engagement portion and an expansion portion, with the length of the wrench part engagement portion along a central axis of the torque wrench body being substantially equal to the length of the wrench part, and the size of an inner hole of the expansion portion being larger than the size of an inner hole of the wrench part engagement portion.

11. The torque wrench for an ultrasonic scalpel according to claim 10, wherein an end face, away from the wrench rotor, of the limiting bulge and an end face, close to the limiting bulge, of the wrench part engagement portion of the wrench rotor are spaced apart by a first distance therebetween along the central axis of the torque wrench body; and an end face, close to the wrench part, of the handle of the ultrasonic scalpel and an end face, away from the handle, of the wrench part are spaced apart by a second distance along the central axis of the torque wrench body, the first distance is greater than the second distance, such that when the ultrasonic scalpel is inserted into the torque wrench in a direction from the end face, away from the wrench rotor, of the limiting bulge to the wrench part, the wrench part is unable to reach the inside of the wrench rotor.

12. An ultrasonic scalpel and torque wrench set, comprising:
an ultrasonic scalpel comprising a handle and a scalpel head, with a wrench part being provided on the scalpel head; and
a torque wrench comprising:
a torque wrench body and a wrench rotor, wherein the torque wrench body comprises a circular-hole-shaped torque hole, with a torque clamping catch being provided in the torque hole, and the wrench rotor being disposed in the torque hole; and the wrench rotor comprises a scalpel head clamping hole, a rotor clamping catch located outside the wrench rotor, and a scalpel head clamping slot located inside the scalpel head clamping hole;
wherein, the wrench part is clamped into the scalpel head clamping slot via the scalpel head clamping hole, the rotor clamping catch is fitted with the torque clamping catch, the torque hole has a cylindrical structure with gradually expanding radius, and the wrench rotor is disposed in an end portion, with a smaller diameter, of the torque hole wherein, the torque wrench body has a cylindrical structure with gradually expanding radius, the cylindrical structure comprises a large end and a small end, the wrench rotor is disposed in the small end, the torque wrench body further comprises a plurality of torque hand-holding portions extending from the small end to the large end, and the plurality of torque hand-holding portions protrude outward from an outer wall of the torque wrench body and are evenly distributed in a circumferential direction with the torque hole as the center; and
an inner wall of the torque hole further comprises a plurality of limiting bulges, the plurality of limiting bulges are evenly distributed in the circumferential direction with the torque hole as the center, and the diameter of the largest circle formed by the plurality of limiting bulges is smaller than the diameter of a handle of the ultrasonic scalpel.

13. The ultrasonic scalpel and torque wrench set according to claim 12, wherein
the torque clamping catch comprises a plurality of unidirectional raised catches protruding from an inner wall of the torque hole to the center of the torque hole, and the plurality of the unidirectional raised catches are annularly distributed on the inner wall of the torque hole.

14. The ultrasonic scalpel and torque wrench set according to claim 13, wherein
two side walls of the unidirectional raised catches are both arc-shaped and gradually converge from the inner wall of the torque hole to the center of the torque hole.

15. The ultrasonic scalpel and torque wrench set according to claim 13, wherein the torque wrench body further comprises a groove corresponding to a gradually changing profile of the unidirectional raised catches and formed on the inner wall of the torque hole.

16. The ultrasonic scalpel and torque wrench set according to claim 15, wherein two side walls of the groove are also arc-shaped and gradually converge in a direction opposite to the direction in which the two side walls of the unidirectional raised catches gradually converge.

* * * * *